(12) United States Patent
Liu et al.

(10) Patent No.: US 12,251,779 B1
(45) Date of Patent: Mar. 18, 2025

(54) PROTECTIVE DEVICE FOR WELDING MACHINE INTERLOCKING, DESIGN METHOD AND SHIELD

(71) Applicant: CHANGZHOU SHINE SCIENCE&TECHNOLOGY CO.LTD., Changzhou (CN)

(72) Inventors: Libin Liu, Changzhou (CN); Feng Sha, Changzhou (CN)

(73) Assignee: CHANGZHOU SHINE SCIENCE & TECHNOLOGY CO.LTD., Changzhou (CN)

(*) Notice: Subject to any disclaimer, the term of this patent is extended or adjusted under 35 U.S.C. 154(b) by 0 days.

(21) Appl. No.: 18/818,506

(22) Filed: Aug. 28, 2024

Related U.S. Application Data

(63) Continuation of application No. PCT/CN2024/094355, filed on May 21, 2024.

(30) Foreign Application Priority Data

Nov. 8, 2023 (CN) .......................... 202311478005.0

(51) Int. Cl.
*B23K 37/00* (2025.01)
*A61F 9/06* (2006.01)
*B23K 37/006* (2025.01)

(52) U.S. Cl.
CPC ............ *B23K 37/006* (2013.01); *A61F 9/061* (2013.01)

(58) Field of Classification Search
CPC .............................. B23K 37/006; A61F 9/061
See application file for complete search history.

(56) References Cited

U.S. PATENT DOCUMENTS

| 2017/0372216 | A1* | 12/2017 | Awiszus | A61F 11/06 |
| 2017/0374436 | A1* | 12/2017 | Awiszus | A62B 18/00 |
| 2019/0175961 | A1* | 6/2019 | Awiszus | A61F 9/067 |
| 2021/0052427 | A1* | 2/2021 | Awiszus | A62B 18/00 |

FOREIGN PATENT DOCUMENTS

| CN | 114419659 A | 4/2022 |
| CN | 114581810 A | 6/2022 |
| CN | 219835752 U | 10/2023 |

* cited by examiner

*Primary Examiner* — Charles R Kasenge
(74) *Attorney, Agent, or Firm* — George D. Morgan

(57) ABSTRACT

The invention relates to the technical field of welding machine protection, specifically a protective device for interlocking welding machines, a design method, and a shield. The device includes: an inductive detection module to detect the relative position between the shield and a human head; a position detection module to detect the filter lens position relative to the shield; a determination module connected to both detection modules to check if all parameters are within a preset range, converting them into an unlocking signal if so; and a transmission module to send this signal to the welding machine, allowing operator control after unlocking. The invention enhances safety, reduces injury risks, and offers reliable protection, with advantages like high safety, automatic control, and effective interlocking.

7 Claims, 4 Drawing Sheets

PROTECTIVE DEVICE FOR WELDING MACHINE INTERLOCKING, DESIGN METHOD AND SHIELD

CROSS-REFERENCE TO RELATED APPLICATIONS

The application claims priority to Chinese patent application No. 2023114780050, filed on Nov. 8, 2023, the entire contents of which are incorporated herein by reference.

TECHNICAL FIELD

The invention relates to the technical field of welding machine protection, in particular to a protective device for welding machine interlocking, a design method and a shield.

BACKGROUND

Welding technology is a manufacturing and processing technique that involves joining two or more materials together through heat, pressure, or chemical processes to form a single structure or component. Welding technology is commonly used in manufacturing, construction, maintenance, and other fields to create strong connections, ensuring the stability and performance of structures. This technology encompasses various methods including arc welding, gas shielded welding, laser welding, spot welding, plasma welding, ultrasonic welding, etc. Each method has its specific applications and advantages. Welding technology plays a crucial role in the manufacturing and construction industries, enabling the connection of various structures and components, thus facilitating the production and maintenance of a wide range of products.

As welding is applied to more scenarios, welding shields have also become more diverse. These welding shields feature movable filter lenses that filter out harmful light to protect the eyes of the wearer. The welding shield effectively prevents damage to the eyes and face from welding sparks, achieving the goal of comprehensive protection.

Currently, most welding shields are independent of welding machines. Welding machines can perform welding operations any time. However, if the welding shield is not worn correctly, such as not wearing it at all or not positioning the filter lens correctly, it can cause damage to the eyes and face, posing significant safety hazards.

The information disclosed in Background Art is only intended to facilitate the understanding of the general background of the invention, and should not be taken as an acknowledgement or any form of implication that this information constitutes the prior art known to those of ordinary skill in the art.

SUMMARY

The invention provides a protective device for welding machine interlocking, a design method and a shield, to solve the problems pointed out in the background art.

To achieve the above objective, the invention adopts the following technical scheme.

A protective device for welding machine interlocking comprises:
an inductive detection module configured to detect relative position parameters between a shield and a human head;
a position detection module configured to detect position parameters of a filter lens relative to the shield;
a determination module connected with the inductive detection module and the position detection module and configured to determine whether detection parameters of the inductive detection module and the position detection module are all within a preset range, if so, convert the detection parameters into an unlocking signal, and if not, continue the detection; and
a transmission module connected with the determination module and configured to transmit the unlocking signal to a welding machine to unlock the welding machine, enabling an operator to control the welding machine after unlocking.

Further, the inductive detection module detects the relative position parameters between the shield and the human head through at least one of an ultrasonic ranging sensor, a photoelectric switch sensor, a capacitive detection sensor and an infrared sensor.

Further, the position detection module detects the position parameters of the filter lens through at least one of a Hall position sensor, a mechanical switch and a photoelectric switch.

The protective device for welding machine interlocking further comprises a warning module and an operation action acquisition module;
the operation action acquisition module acquires operation actions of the operator on the welding machine and outputs an operation signal; and
the warning module receives the operation signal from the operation action acquisition module and a determination result from the determination module, and outputs a warning signal when the operation signal is received and the determination result is negative.

Further, the warning signal is at least one of alarm sound, light flashing and display screen information.

Further, the warning module further comprises a deactivation unit for manually deactivating the warning signal.

Further, the determination module further comprises a voice broadcasting unit for converting a determination signal into a voice signal.

The invention further provides a design method of the protective device for welding machine interlocking, comprising:
collecting data and combining the data into a data set, the data comprising relative position data of different welders' heads and shields;
labeling each datum in the data set to indicate whether a relative position is correct;
extracting features related to the relative positions of the shields and the human heads from each datum; training a support vector machine model by using the labeled data set, the support vector machine model being used for classifying data to predict whether the relative position is correct; and
establishing a work association between a correct position and the inductive detection module to ensure the accurate functioning of the determination module.

Further, the support vector machine model comprises:
an input layer for inputting the labeled data set;
at least three SVM models, with at least one configured to detect data anomalies, at least one configured to suppress data noise, and at least one configured to filter out irrelevant data;
an ensemble learning hierarchy for integrating the plurality of SVM models to synthesize the results of each SVM model through an ensemble learning method to generate a final decision; and an output layer for mapping a final integration result into a classification label to predict whether a relative position is correct.

The invention further provides a shield which adopts the protective device for welding machine interlocking as described above, realizing the unlocking of the welding machine, and allowing the operator to control the welding machine after unlocking.

Through the technical scheme of the invention, the following technical effects can be achieved.

According to the invention, by arranging the inductive detection module, the position detection module, the determination module and the transmission module, only when the detection parameters of the inductive detection module and the position detection module are within the preset range, the unlocking signal will be transmitted to the welding machine, the welding machine can be controlled, and the protective device can automatically unlock the welding machine by transmitting the unlocking signal. In this way, it ensures safe operation, provides a more reliable protective effect, reduces potential injury risks, and has the advantages of high safety, automatic control, and welding machine interlocking, effectively improving the safety and reliability of welding operations.

BRIEF DESCRIPTION OF DRAWINGS

In order to more clearly explain the embodiments of the invention or the technical scheme in the prior art, the following will briefly introduce the drawings needed in the description of the embodiments or the prior art. Obviously, the drawings in the following description are only some embodiments of the invention. For those of ordinary skill in the art, other drawings can be obtained according to the provided drawings without paying creative labor.

DETAILED DESCRIPTION OF THE EMBODIMENTS

The technical schemes in the embodiments of the present invention are clearly and completely described in the following with reference to the drawings in the embodiments of the present invention. It is obvious that the described embodiments are only some of the embodiments of the present invention and are not all the embodiments thereof.

Unless otherwise defined, all technical terms and scientific terms used herein have the same meanings as commonly understood by those skilled in the technical field of the invention. The terms used in the specification of the invention are only for the purpose of describing specific embodiments. are not intended to limit the invention. As used herein, the term "and/or" includes any and all combinations of one or more related listed items.

Embodiment I

Figure 1:
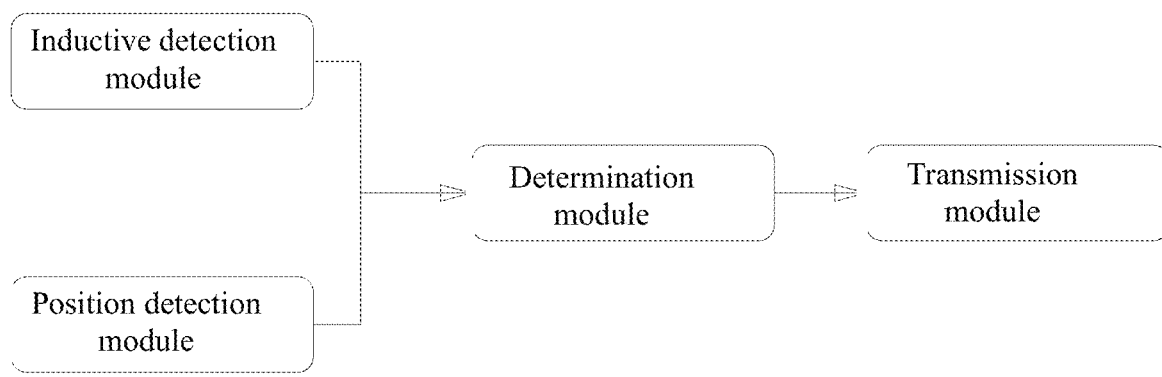
FIG. 1 is a frame diagram of a protective device for welding machine interlocking.
Figure 2:
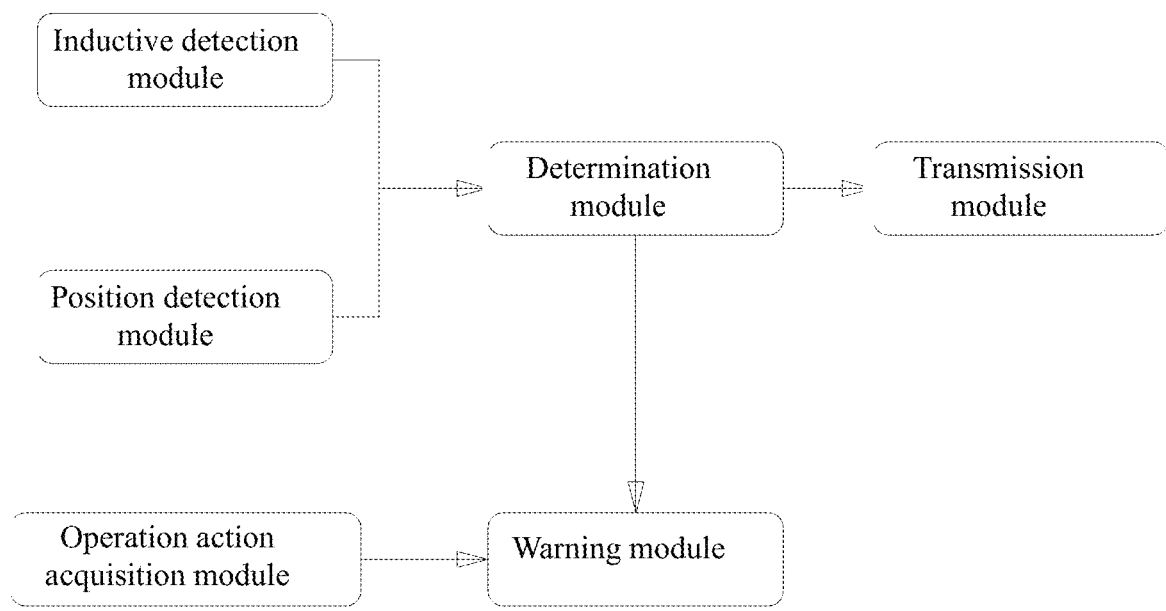
FIG. 2 is an optimized frame diagram of a protective device for welding machine interlocking.
Figure 3:
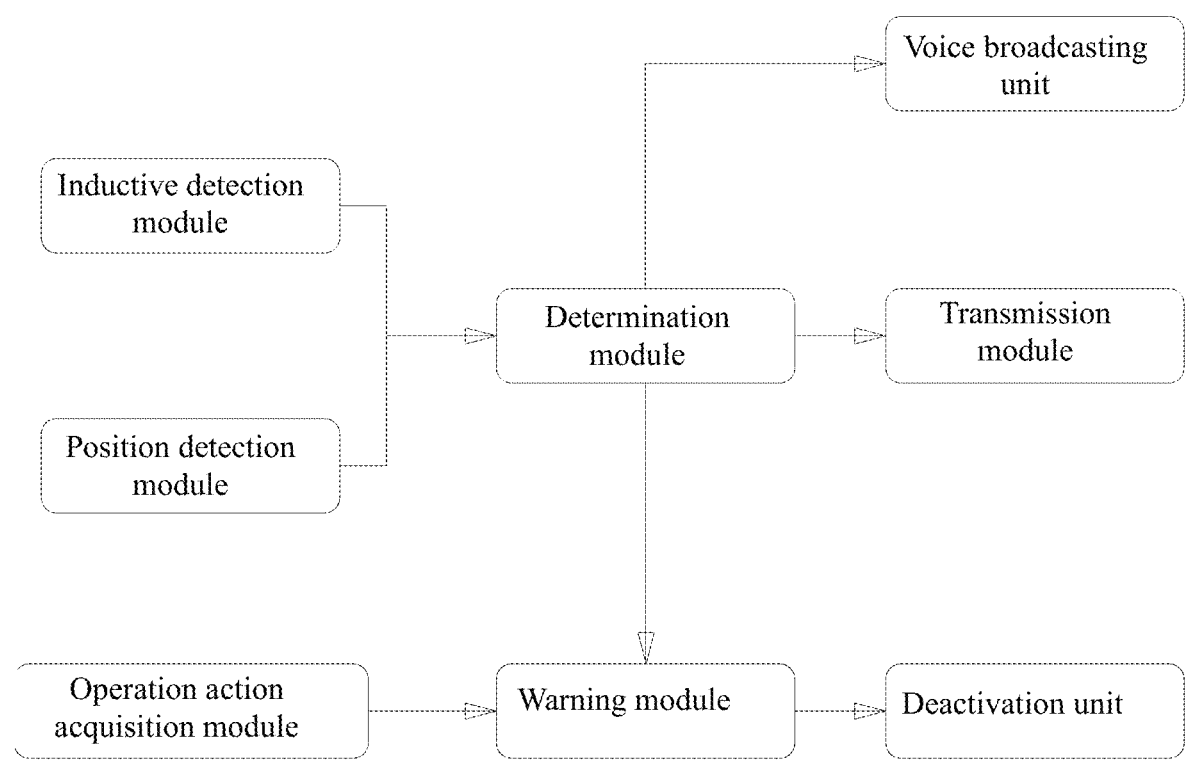
FIG. 3 is another optimized frame diagram of a protective device for welding machine interlocking.

As shown in FIGS. 1-3, a protective device for welding machine interlocking comprises:

an inductive detection module configured to detect relative position parameters between a shield and a human head, where through the relative position detection, whether the shield is worn can be detected, so as to ensure that welders wear the shield correctly during welding, thereby providing necessary safety protection and reducing the potential injury risk, and the relative position detection can be realized by various sensors;

a position detection module configured to detect position parameters of a filter lens relative to the shield, so as to detect whether the filter lens is in a correct protective position relative to the shield, thereby effectively shielding harmful light and providing a more reliable protective effect;

a determination module connected with the inductive detection module and the position detection module and configured to determine whether detection parameters of the inductive detection module and the position detection module are all within a preset range, if so, convert the detection parameters into an unlocking signal, and if not, continue the detection, where the condition of "not" signifies that the detection parameters of one or both of the inductive detection module and the position detection module are not within the preset range and will not be converted into an unlocking signal, so the welding machine will not receive any unlocking signal and will not be unlocked for the user to operate; and a transmission module connected with the determination module and configured to transmit the unlocking signal to a welding machine to unlock the welding machine, enabling an operator to control the welding machine after unlocking. In this embodiment, the signal transmission mode of the transmission module may be wired transmission, for example, through a wired aviation plug, or wireless transmission, for example, through Wi-Fi communication and Bluetooth communication.

According to the invention, by arranging the inductive detection module, the position detection module, the determination module and the transmission module, only when the detection parameters of the inductive detection module and the position detection module are within the preset range, the unlocking signal will be transmitted to the welding machine, the welding machine can be controlled, and the protective device can automatically unlock the welding machine by transmitting the unlocking signal. In this way, it ensures safe operation, provides a more reliable protective effect, reduces potential injury risks, and has the advantages of high safety, automatic control, and welding machine interlocking, effectively improving the safety and reliability of welding operations.

Preferably, the inductive detection module detects the relative position parameters between the shield and the human head through at least one of an ultrasonic ranging sensor, a photoelectric switch sensor, a capacitive detection sensor, an infrared sensor or other inductive sensors.

Specifically, the ultrasonic ranging sensor is a product used to measure the distance. By sending and receiving ultrasonic waves, the distance from a module to an obstacle in front can be calculated by using the time difference and sound propagation speed. Therefore, the distance between the shield and the human head can be measured by the ultrasonic ranging sensor, and one or more groups of detection points can be set correspondingly here. This distance parameter can be used to determine whether the shield is correctly worn on the human face. Regarding the use of photoelectric switch sensors, a direct reflection method can be employed, where a transmitter and a receiver are integrated as a single unit. When worn, the light emitted by the transmitter directly shines on the human head, and the detection is based on the changes in reflected light. Alternatively, a through-beam method can be used, involving a configuration with a transmitter and a receiver placed opposite each other. The light emitted by the transmitter is directed towards the receiver, creating a closed optical path between them. When worn, the detection is based on the interruption of light in the optical path. In the case of capacitive detection sensors, the operating principle is based on the existence of capacitance between any two conductive objects. One terminal (TOUCH) of the sensor can form a capacitance with the ground. When the shield is not worn, the surrounding environment is considered to be in a constant state, and the capacitance value remains fixed and small. However, when the shield is worn and a human body approaches a detection terminal of the sensor, the capacitance formed between the human body and the ground in parallel with the capacitance formed between the TOUCH terminal and the ground results in an increase in the total capacitance value. When infrared detectors are used, whether the shield is worn can be determined by detecting the radiant heat energy of the human head.

When using the aforementioned sensors, it is possible to choose a single type for usage, and the quantity used can be flexibly selected. However, in order to optimize costs, it is more favorable to use as few sensors as possible while still meeting the usage requirements. Alternatively, a combination of two or more types can be used. In this case, different types of sensors can serve as backups for each other or be used as references, leading to more accurate results. The quantity selection for each type of sensor is also flexible, and all combinations of quantities fall within the scope of protection of this invention.

In this embodiment, the position detection module detects the position parameters of the filter lens through at least one of a Hall position sensor or other position sensors, a mechanical switch, a photoelectric switch or other switches.

The Hall voltage varies with the intensity of the magnetic field, the stronger the magnetic field, the higher the voltage, and the weaker the magnetic field, the lower the voltage, typically only a few millivolts. However, when amplified by an amplifier in an integrated circuit, this voltage can be large enough to output a stronger signal. Specifically, a Hall element can be arranged on a built-in motherboard of the position detection module, and a ferromagnetic element can be arranged on a rotating mechanism capable of changing the position of the shield. When the relative position of the filter lens relative to the shield changes, if the distance between the Hall element and the ferromagnetic element becomes larger, the generated Hall voltage value will be smaller, and when the distance gets smaller, the Hall voltage value will be larger. By collecting the current voltage value in real time, it can be considered that the filter lens has reached a specified position once a certain voltage value is reached. The working principle of mechanical switches is simpler. Whether the mechanical switch is on or not can be used as a criterion for determining whether the filter lens reaches the use position. The photoelectric switch continuously monitors received optical signals, enabling the system to detect the position parameters of the filter lens in real time and provide appropriate control and feedback. This approach ensures that the filter lens operates in the correct position, enhancing detection accuracy and stability.

Similarly, in this optimization scheme, one of a Hall position sensor or other position sensors, a mechanical switch, a photoelectric switch or other switches can be selected for use, and the quantity used in this case can be flexibly selected. Alternatively, a combination of two types can be used. In this case, different types of sensors can serve as backups for each other or be used as references. The quantity selection for each type of sensor is also flexible, and all combinations of quantities fall within the scope of protection of this invention.

In the above preferred scheme, the selection of relevant sensors in the inductive detection module and the position detection module is described. Besides the various types of sensors mentioned, other types of sensors or schemes that can realize the detection of position parameters in the present invention are also within the scope of protection of the invention.

The protective device for welding machine interlocking further comprises a warning module and an operation action acquisition module;

the operation action acquisition module acquires operation actions of the operator on the welding machine and outputs an operation signal, and the operation actions here mainly include starting and adjusting the parameters of the welding machine; and the warning module receives the operation signal from the operation action acquisition module and a determination result from the determination module, and outputs a warning signal when the operation signal is received and the determination result is negative.

In this preferred scheme, there are at least two reception scenarios for operation signals.

In the first case, the received signal is a start-up signal, and the welding machine is in a closed state. If the determination result is negative, it indicates that the shield has not been worn properly, and it is dangerous to start the welding machine at this point. Of course, based on the above scheme of the invention, the start-up action cannot be realized at this point because it is not unlocked. According to this preferred scheme, in this case, an alert is issued to the operator to make it clear that the starting action cannot be carried out due to improper wearing.

In the second case, the received signal is a welding machine parameter adjustment signal. In this case, if the welding machine is not started, it is considered an operator error and can be overlooked, as the inactivity of the welding machine does not pose any danger. However, if the welding machine is active and the operator intends to adjust the parameters, this presents an opportunity to check for any displacement of the shield during work. Therefore, the determination result is identified again. If the determination result is negative at this point, it indicates that the shield has shifted position during welding. Adjusting the parameters at this point could lead to occupational injuries due to changes in the visibility of the operator's eyes caused by the change in light conditions. Therefore, in this preferred scheme, the operator is alerted to readjust the wearing position before resuming welding work. Of course, this scenario is less likely to occur in practice, as the operator can usually directly recognize the displacement. However, there is a need for warning in situations where the shield has shifted, resulting in a negative determination result from the determination module, yet has not yet affected the operator's welding process. This preferred scheme provides timely warnings in such cases to facilitate quick position correction, preventing the accumulation of displacement that could cause instantaneous harm.

Preferably, the warning signal is at least one of alarm sound, light flashing and display screen information.

Specifically, the warning signal can trigger an alarm device and send out an audible alarm to attract the attention of the operator. a warning unit can also flash warning lights on a control panel or equipment by controlling lights or indicator lamps to remind the operator of abnormal conditions. The warning unit can also display relevant warning information on a display screen, such as warning icons, text prompts, etc., so that the operator can immediately perceive the problem, wear the shield in time and rotate the filter lens to the correct position, thus reducing the harm to the operator. The above methods can be used alternatively or in combination to achieve better warning effects.

In this embodiment, the warning module further comprises a deactivation unit for manually deactivating the warning signal.

The deactivation unit allows the operator to manually deactivate the warning signal under certain circumstances. In some cases, the warning signal may produce false alarms, causing frequent disturbances to operators and reducing work efficiency. Through the deactivation unit, the operator can deactivate false warning signals, preventing unnecessary disruptions and maintaining a regular work pace. The deactivation unit provides a mechanism for manual assessment and risk control. Operators can decide whether to deactivate the warning signal according to their own experience and judgment, so as to better adapt to the specific working environment and needs. In this way, operators can manage risks reasonably and take appropriate measures to protect their own safety when necessary. The deactivation unit highlights the decision-making power of the operator in safety management. This can facilitate effective interaction between the operator and the protective device, enabling a better awareness of the system's status, and allowing for flexible handling and response to different scenarios.

The determination module further comprises a voice broadcasting unit for converting a determination signal into a voice signal.

Specifically, for example, when the shield has been worn and the filter lens is in the correct position, a voice prompt will indicate that the shield and the filter lens have been worn properly, and welding work can proceed; when the shield is not worn, a voice prompt will instruct to wear the shield; when the filter lens is not in the correct position, a voice prompt will instruct to adjust the filter lens; and when the shield is not worn and the filter lens is not in the correct position, a voice prompt will instruct to wear the shield and adjust the filter lens. The voice broadcasting unit can convert the determination result into the voice signal in real time and transmit information to the operator by voice. In this way, the operator can directly hear the corresponding warning or prompt without relying on other visual instructions, and real-time and clear instructions and warning messages can be provided through voice communication to enhance the safety and efficiency of welding operations.

Embodiment II

Figure 4:
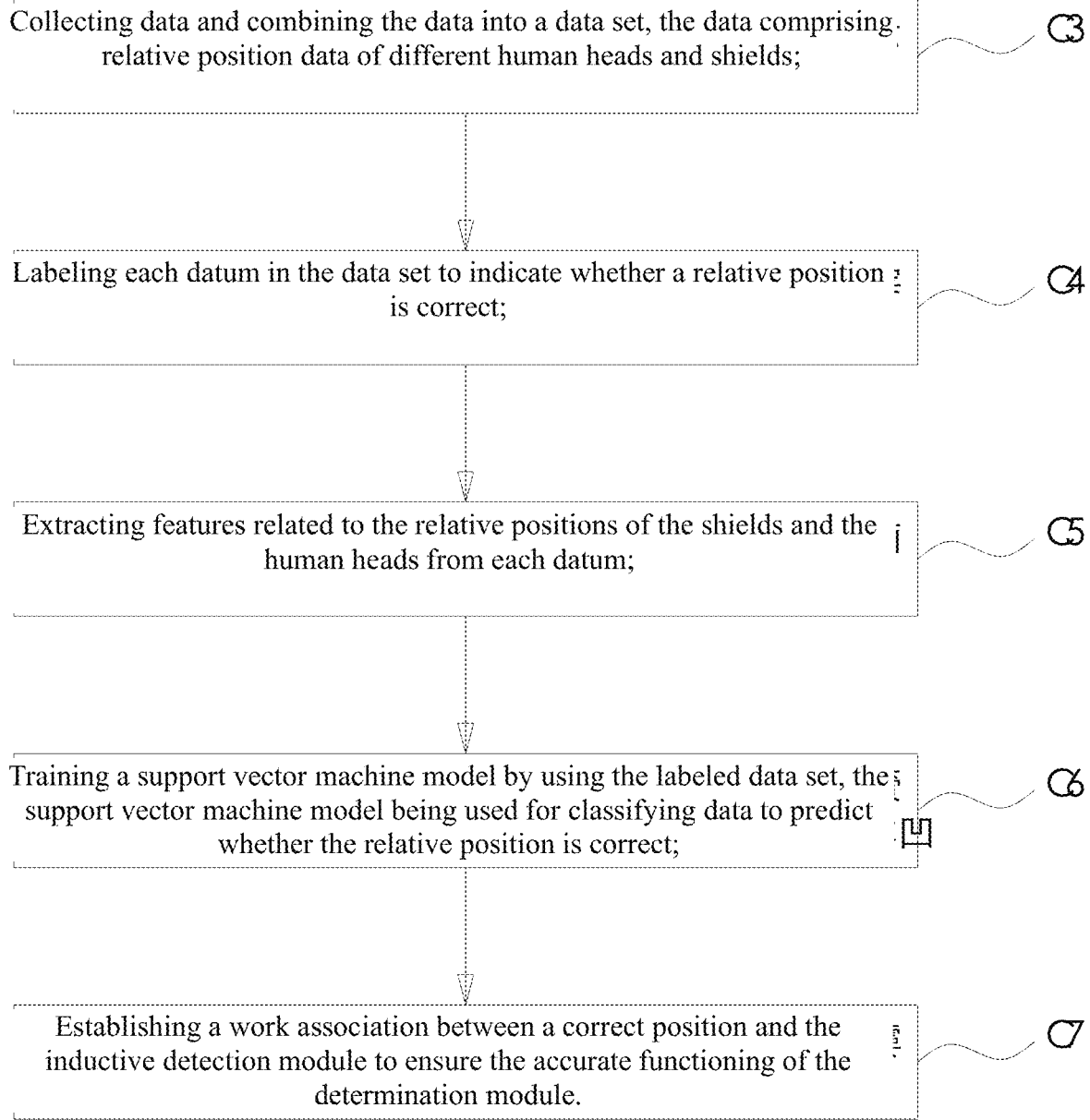
FIG. 4 is a flowchart of a design method of a protective device for welding machine interlocking.

In this embodiment, as shown in FIG. 4, an optimized design method is provided as follows.

The invention further provides a design method of the protective device for welding machine interlocking, comprising:

A1, collecting data and combining the data into a data set, the data comprising relative position data of different welders' heads and shields, where the above data can be collected by simulating the actual operation situation or in the real welding environment;

A2, labeling each datum in the data set to indicate whether a relative position is correct, where labeling may involve binary tags, such as "correct" or "incorrect," or may be more specific, such as specifying the range of errors;

A3, extracting features related to the relative positions of the shields and the human heads from each datum, where the features may include sensor measurements, angles, distances or other related parameters, as well as other environmental factors, such as lighting conditions;

A4, training a support vector machine model by using the marked data set, the support vector machine model being used for classifying data to predict whether the relative position is correct; and A5, establishing a work association between a correct position and the inductive detection module to ensure the accurate functioning of the determination module.

Before training the support vector machine model, data preprocessing is required, which includes standardizing or normalizing the data to ensure that all features are on the same scale. It is also possible to perform data segmentation, dividing the dataset into a training set and a test set for model validation. Using the training data set, the support vector machine model is trained to learn how to associate the input features with the labels of relative positions. The goal of the support vector machine model is to find a decision boundary and separate different categories of data, which represent different relative positions. Specifically, when the shield is properly worn, the data measured by the sensor will belong to one category, while when the shield is not properly worn, the data will belong to another category. The decision boundary is a hyperplane determined by the support vector machine model, which produces two categories in a feature space. In the present invention, the feature space includes various parameters extracted from the sensor measurement, such as distance, angle, illumination intensity, capacitance value, etc. The support vector machine model tries to find this decision boundary, so as to separate data points related to proper wearing from data points related to improper wearing.

In the implementation process, once this decision boundary is found, the support vector machine model can be used to predict new data points, that is, to determine whether the shield is worn properly according to the features measured by the sensors. The new data located on one side of the decision boundary will be classified into one category, and the new data on the other side will be classified into another category.

It is essential to know whether the shield is properly worn. In the implementation process, if the shield is not properly worn, the inductive detection module may not be able to accurately measure the relevant parameters, as it fails to make effective contact with the welder's head or is improperly positioned. This can result in measurement inaccuracies, misjudgments, or malfunction, thereby compromising the reliability and safety of the protective device. In this preferred scheme, the use of the support vector machine allows for the determination of whether the shield is correctly worn, and two categories ("correct" and "incorrect") can be determined based on sensor data and features. Once it is determined whether the shield is properly worn, this information can be associated with the operation of the inductive detection module.

Specifically, when the inductive detection module detects that the welder is wearing the shield properly, it is known that the relevant parameter data are reliable, and these data can be used to carry out safety monitoring and control the operation of the welder, which means that the inductive detection module can safely use the sensor data to perform its tasks.

Preferably, the support vector machine model comprises:
an input layer for inputting the labeled data set;
at least three SVM models, with at least one configured to detect data anomalies, at least one configured to suppress data noise, and at least one configured to filter out irrelevant data;
an ensemble learning hierarchy for integrating the plurality of SVM models to synthesize the results of each SVM model through an ensemble learning method to generate a final decision; and
an output layer for mapping a final integration result into a classification label to predict whether a relative position is correct.

In the implementation process, it is necessary to train several different SVM models through labeled data sets, each model is used for different tasks, such as detecting abnormal situations, suppressing noise or filtering out irrelevant data, and it is also necessary to ensure that each model performs well on its specific tasks. For given input data, determination results are generated correspondingly by each SVM model, which may be a category label (such as "correct" or "incorrect") or a probability value, depending on the output type of each model.

In the implementation process, it is necessary to choose appropriate ensemble learning methods for the ensemble learning hierarchy. Common ensemble learning methods include voting, weighted voting, average output, etc. In the implementation process, we will consider a scenario involving only three SVM models and weighted voting. It specifically comprises:

S1, training three different SVM models, where each model is used for performing a specific task, and it is ensured that each model performs well on its specific task;

S2, generating determination results of each model;
where the first SVM model is configured to detect data anomalies, and for given input data, the model is used to generate an anomaly detection result, which may be a binary label indicating whether data are abnormal;
the second SVM model is configured to suppress data noise, and the model is used to generate a noise suppression result, which may be a category label of data, indicating whether the data are subjected to noise interference; and
the third SVM model is configured to filter out irrelevant data, and this model is used to generate a data filtration result, which may produce a category label of data to indicate whether the data are related to the problem;

S3, assigning weights to each model, where in order to perform weighted voting, a weight is assigned to each model, the weight reflects the performance of the model on its specific task, and generally, the model with better performance gets higher weight;

S4, calculating a weighted score;
where for the first anomaly detection model, the determination result is multiplied by the corresponding weight;
for the second noise suppression model, the determination result is also multiplied by the corresponding weight; and
for the third data filtration model, the determination result is also multiplied by the corresponding weight;

S5, synthesizing the results of each model, where a final weighted score is determined by adding the weighted scores of each model, and the final score can be used to predict whether the relative position is correct;

S6, setting a threshold, where the threshold is set to determine a critical point of the weighted score, and the result exceeding the threshold is classified as correct, otherwise it is classified as incorrect; and S7, evaluation and verification, where it is necessary to make sure that before the weighted voting, each model is verified and evaluated to understand their performance on their respective tasks, and the whole weighted voting system is verified to ensure that it performs well in practical application.

In this embodiment, the relative position data of different welders' heads and shields are collected and the data set is labeled to determine whether the relative position is correct, which makes the data for training the model more comprehensive and accurate, thus improving the performance and accuracy of the model; and the support vector machine is used as a classification model, which has excellent generalization ability and adaptability, can effectively deal with high-dimensional data, and is suitable for multi-category classification and anomaly detection tasks. In the implementation process, at least three SVM models are introduced, and each model is aimed at different tasks, including detecting abnormal data, suppressing data noise and filtering out irrelevant data. This multi-model integration method increases the robustness of the system and the probability of correct judgments. Finally, the results of multiple SVM models are synthesized by the ensemble learning hierarchy. Through the ensemble learning method, the accuracy of judgments can be further enhanced, aiding in addressing multi-task integration problems and ensuring the collaboration of multiple models. Through the above scheme, the work association between the correct position and the inductive detection module is established, which ensures accurate judgments during work. In this way, when the welder wears the shield correctly, the inductive detection module can trust the sensor data and perform its task, thus improving the reliability and safety of the protective device.

Embodiment III

In this embodiment, an application scenario of the protective device for welding machine interlocking is given as follows.

The invention further provides a shield which adopts the protective device for welding machine interlocking as described above, realizing the unlocking of the welding machine, and allowing the operator to control the welding machine after unlocking.

The technical effects that the shield in this embodiment can achieve are as described in the above embodiments, which will not be repeated here.

The basic principles, main features and advantages of the invention are described above. Those skilled in the art should understand that the invention is not limited by the above-mentioned embodiments. What is described in the above-mentioned embodiments and the description is only to illustrate the principles of the invention. Without departing from the spirit and scope of the invention, the invention will have various changes and improvements, which all fall within the scope of the claimed invention. The protection scope of the invention is defined by the appended claims and their equivalents.

What is claimed is:

1. A design method of a protective device for welding machine interlocking, comprising a protective device for welding machine interlocking;

wherein the protective device for welding machine interlocking comprises:

an inductive detection module configured to detect relative position parameters between a shield and a human head;

a position detection module configured to detect position parameters of a filter lens relative to the shield;

a determination module connected with the inductive detection module and the position detection module and configured to determine whether detection parameters of the inductive detection module and the position detection module are all within a preset range, if so, convert the detection parameters into an unlocking signal, and if not, continue the detection; and a transmission module connected with the determination module and configured to transmit the unlocking signal to a welding machine to unlock the welding machine, enabling an operator to control the welding machine after unlocking;

the design method of the protective device for welding machine interlocking comprises:

collecting data and combining the data into a data set, the data comprising relative position data of different welders' heads and shields;

labeling each datum in the data set to indicate whether a relative position is correct;

extracting features related to the relative positions of the shields and the human heads from each datum;

training a support vector machine model by using the labeled data set, the support vector machine model being used for classifying data to generate a prediction result indicating whether the relative position is correct; and establishing an association between the prediction result and the inductive detection module by using the prediction result; and the support vector machine model comprises:

an input layer for inputting the labeled data set;

at least three SVM models, with at least one configured to detect data anomalies, at least one configured to suppress data noise, and at least one configured to filter out irrelevant data;

an ensemble learning hierarchy for integrating the plurality of SVM models to synthesize the results of each SVM model through an ensemble learning method to generate a score; and an output layer mapping the score into a classification label based on a threshold, wherein the score exceeding the threshold is classified as correct, otherwise the score is classified as incorrect, and the output layer generate the prediction result indicating based on the classification label.

2. The design method of the protective device for welding machine interlocking according to claim 1, wherein the inductive detection module detects the relative position parameters between the shield and the human head through at least one of an ultrasonic ranging sensor, a photoelectric switch sensor, a capacitive detection sensor and an infrared sensor.

3. The design method of the protective device for welding machine interlocking according to claim 1, wherein the position detection module detects the position parameters of the filter lens through at least one of a Hall position sensor, a mechanical switch and a photoelectric switch.

4. The design method of the protective device for welding machine interlocking according to claim 1, further comprising a warning module and an operation action acquisition module;

wherein the operation action acquisition module acquires operation actions of the operator on the welding machine and outputs an operation signal; and the warning module receives the operation signal from the operation action acquisition module and a determination result from the determination module, and outputs a warning signal when the operation signal is received and the determination result is negative.

5. The design method of the protective device for welding machine interlocking according to claim 4, wherein the warning signal is at least one of alarm sound, light flashing and display screen information.

6. The design method of the protective device for welding machine interlocking according to claim 4, wherein the warning module further comprises a deactivation unit for manually deactivating the warning signal.

7. The design method of the protective device for welding machine interlocking according to claim 1, wherein the determination module further comprises a voice broadcasting unit for converting a determination signal into a voice signal.

* * * * *